United States Patent
Sutherland et al.

[11] Patent Number: 6,126,639
[45] Date of Patent: Oct. 3, 2000

[54] CONTINUOUS AMBULATORY PERITONEAL DIALYSIS CATHETER SUPPORT UNDERGARMENT

[76] Inventors: Joanne M. Sutherland; Brian M. Sutherland, both of 2595 Lakeside Dr., Tobyhanna, Pa. 18466-3713

[21] Appl. No.: 09/196,468

[22] Filed: Nov. 19, 1998

Related U.S. Application Data

[63] Continuation-in-part of application No. 08/517,379, filed as application No. PCT/US96/11696, Jul. 15, 1996, Pat. No. 5,839,946
[60] Provisional application No. 60/073,824, Feb. 5, 1998.
[51] Int. Cl.$^7$ ............................................. A61M 5/32
[52] U.S. Cl. ............................. 604/179; 128/DIG. 26; 2/338
[58] Field of Search ........................... 604/174, 179; 128/DIG. 26; 2/338, 311

[56] References Cited

U.S. PATENT DOCUMENTS

| | | | |
|---|---|---|---|
| 4,531,942 | 7/1985 | Turner | 604/180 |
| 4,738,661 | 4/1988 | Marut . | |
| 4,781,200 | 11/1988 | Baker | 128/670 |
| 4,955,867 | 9/1990 | Endo . | |
| 5,344,406 | 9/1994 | Spooner | 604/179 |
| 5,403,285 | 4/1995 | Roberts | 604/179 |
| 5,425,719 | 6/1995 | Lessing, Jr. . | |
| 5,468,229 | 11/1995 | Chandler . | |
| 5,496,282 | 3/1996 | Militzer et al. . | |
| 5,688,248 | 11/1997 | Lessing, Jr. . | |
| 5,708,978 | 1/1998 | Johnsrud | 2/102 |
| 5,755,698 | 5/1998 | Kagan et al. | 604/179 |
| 5,853,396 | 12/1998 | Bennes et al. | 604/179 |

OTHER PUBLICATIONS

Associated Fabrics Corporation, webstie, www.afcnewyork.com, Aug. 3, 1999.
Associated Fabrics Corporation, Costume Fabric Catalog 1982–83.

*Primary Examiner*—Ronald Stright
*Assistant Examiner*—Jeremy Thissell
*Attorney, Agent, or Firm*—Schnader Harrison Segal & Lewis LLP

[57] ABSTRACT

This invention relates to a continuous ambulatory peritoneal dialysis catheter support undergarment which allows for easy use and comfortable wearing by the patient. Additionally, the undergarment is versatile in that it may be worn virtually undetectable under clothing and is also designed to be sufficiently durable to withstand many washing and drying cycles. The belt also is capable of conforming to the ever changing waistline of a continuous ambulatory peritoneal dialysis patient.

10 Claims, 1 Drawing Sheet

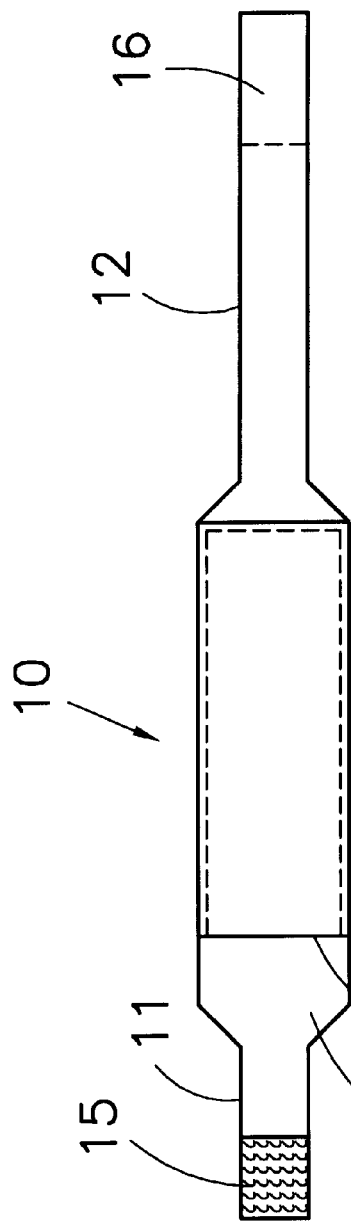
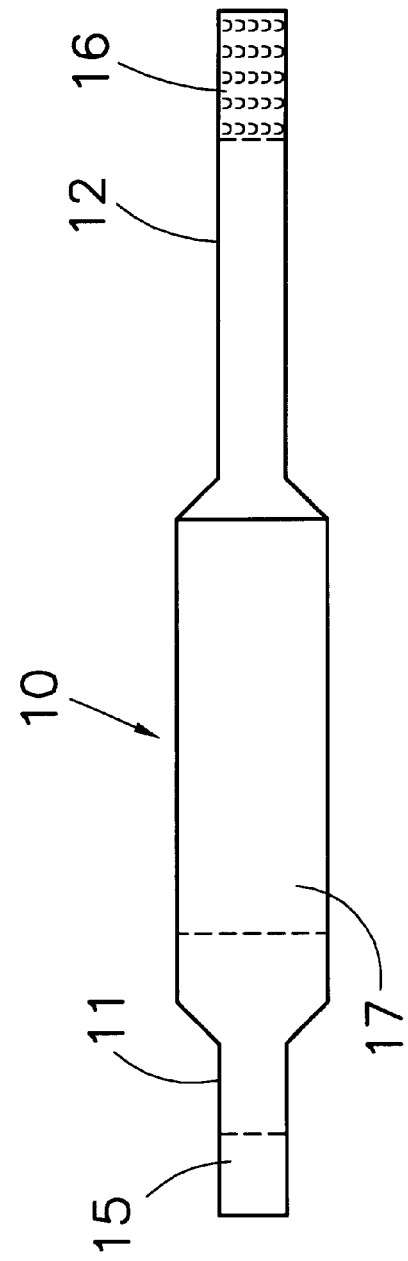

CONTINUOUS AMBULATORY PERITONEAL DIALYSIS CATHETER SUPPORT UNDERGARMENT

This application is a continuation-in-part of application Ser. No. 08/517,379 filed Aug. 21, 1995 now U.S. Pat. No. 5,839,946. This application also claims benefit to U.S. Provisional application No. 60/073,824 filed Feb. 5, 1998, which is a 371national stage entry of PCT/US 96/11696 filed Jul. 15, 1996.

BACKGROUND OF THE INVENTION

1. Field of the Invention

This invention relates generally to the art of continuous ambulatory peritoneal dialysis ("CAPD") support undergarments. The invention particularly relates to an undergarment which comfortably holds in place a CAPD catheter, and can be worn around the abdomen or hips of a CAPD patient, thus allowing versatility in the concealment of the CAPD catheter while achieving a greater sense of confidence and self-esteem for the CAPD patient.

As is known to those familiar with continuous ambulatory peritoneal dialysis, a surgically implanted catheter provides an opening through which dialysis solution can be instilled into the abdominal cavity of a peritoneal dialysis patient. The surgically implanted catheter is normally fabricated from a soft, flexible tube material. When not being used to introduce or remove fluid, the catheter is capped or otherwise closed off at its end. Since movement of the external portion of the catheter can cause irritation and infection at the exit site, the protruding catheter needs to be secured against the patient's body, thus providing greater protection and comfort.

2. Description of the Related Art

To Applicants' knowledge, the typical CAPD patient secures the protruding catheter to their body by utilizing adhesive tape. To access the catheter, the tape must be removed and then reapplied upon completing the dialysis procedure. This repeated removal and reapplication of adhesive tape causes severe irritation and pain in many CAPD patients.

Several prior U.S. patents provide belts for securing to the CAPD patient the implanted peritoneal dialysis catheter exiting from the abdomen of the patient. For example, U.S. Pat. No. 4,955,867, issued to Endo, discloses a peritoneal dialysis catheter protector belt comprising a fabric or paper belt or band, which may be disposable, and which is adapted to be fastened around the abdomen of a patient adjacent to the protruding end of a peritoneal dialysis catheter. The belt is equipped with an open-ended pouch which is located on the outer surface of the belt and into which the end of the catheter may be inserted to enclose and protect the end of the catheter and to prevent it from dangling. The belt is not designed to be worn over, and thus cover, the catheter exit site. Moreover, the patent fails to specifically define any fabrics which may be used to fabricate the belt. Further, Applicants have found that a belt having a single pouch on the outer surface of the belt allows the catheter to work its way out of the pouch as the patient moves about throughout the day. This being due to the fact that the pouch fails to hold the catheter in position against the patient's body.

U.S. Pat. No. 5,468,229, issued to Chandler, discloses a belt for a peritoneal dialysis patient having an aperture for receiving and orienting the protruding portion of an implanted catheter toward a plurality of holders along a outer portion of the belt. Chandler broadly discloses that the belt may be made of an elastic material and is designed so that the catheter is fed through an aperture on the inner surface of the belt and exits the aperture at an outer surface and is then placed into a plurality of holders located on the outside of the belt. Although the belt can be worn over the catheter exit site, the patent requires that the patient feed the catheter through the aperture to the outer surface of the belt, where it is secured. The patent broadly discloses that the belt can be fabricated from "an elastic material", but fails to specifically identify such material.

U.S. Pat. No. 5,496,282, issued to Militzer et al., discloses a belt for stabilizing an implanted peritoneal dialysis catheter exiting from the abdomen of a user. The belt includes a body of elasticized fabric designed to encircle the patient, and includes two fasteners with hook and pile features, and a receptacle located on the outer surface of the belt. The belt also includes two fasteners for securing the catheter to the outer portion of the belt. The belt is not designed to be worn over the catheter exit site. Further, although the belt is disclosed as including an elastic material, the patent fails to specifically identify such material.

The subject matter of each of the above U.S. patents is herein incorporated by reference.

It is an object of the present invention to overcome the deficiencies of the prior art by providing a catheter support undergarment which is manufactured from carefully selected expandable material. The undergarment also provides for extremely easy and convenient use by providing a pocket on the inner surface of the undergarment and a fastening and unfastening means which is located at the patient's side when the undergarment is worn. This allows the patient to easily insert the catheter into the pocket and simply wrap the ends of the undergarment around either their waist or hips and attach the ends together at their side. Many CAPD patients are elderly and may have difficulty fastening an undergarment at the back and also may have difficulty feeding the catheter through an aperture or the like to a pocket or securing means on the outer surface of the garment. By locating the pocket at the inner surface of the undergarment, the undergarment also serves to hold the catheter in place against the patient's body. Also, by providing the pocket on the inner surface of the undergarment, the patient is able to completely cover the catheter exit site, thus protecting the site from rubbing against outer garments, belts and the like, while at the same time providing a layer of fabric between the patient's skin and the catheter.

SUMMARY OF THE INVENTION

In accordance with aspects of this invention, it has been found that a catheter support undergarment may be provided for a peritoneal dialysis patient wherein the undergarment comprises a pocket portion located on the inner surface of the belt as well as a first end portion and a second end portion, each having thereon proximate the distal edge of the end portion, cooperating attaching means, such as hook and loop fastening materials. The first and second end portions of the undergarment are provided such that one end portion is shorter in length than the other end portion so that when the undergarment is placed in position such that the catheter is placed within the pocket, the distal edge of each end portion will be located on one side of the patient.

As is well known to those in the art, during treatments, the peritoneal dialysis patient experiences a certain degree of swelling, which results in an expanding waistline. The undergarment of the present invention is able to adjust to this changing condition by fabricating the undergarment from a material capable of easily expanding and contracting, thus comfortably conforming to the changing waistline of the patient during the time the solution dwells in the peritoneal cavity, yet remain tight enough against the body to hold the catheter in place.

BRIEF DESCRIPTION OF THE DRAWINGS

FIG. 1 is a perspective representation of the undergarment of the present invention showing the inner surface of the undergarment;

FIG. 2 is perspective representation of the belt of the present invention, showing the outer surface of the undergarment.

DETAILED DESCRIPTION OF THE INVENTION

In accordance with the present invention, an undergarment is provided which is capable or supporting and substantially completely covering the catheter of a CAPD patient. The undergarment comprises an expandable material having an inner surface, an outer surface, a first end portion and a second end portion. The inner surface of the belt is provided with a pocket for receiving the catheter. The first end portion and the second end portion of the undergarment are designed so that one end portion is longer in length than the other, such that when the undergarment is positioned on and wrapped around the patient, the first and second end portions of the undergarment will be located on the side of the patient. A better understanding of the invention will be apparent with reference to the Figures.

FIG. 1 is a perspective view of the inner surface of the undergarment 10 of the present invention. As can be seen, the undergarment 10 is provided with a pocket 14 located at the inner surface 13 of the undergarment. The undergarment additionally includes a first end portion 11 and a second end portion 12. The first end 11 is provided with a distally located fastening means 15. The second end portion 12 is provided with a distally located corresponding fastening means 16. In FIG. 1, first end portion 11 is shown as being shorter in length than second end portion 12, such that when the catheter is inserted into pocket 14 at the front of the patient, end portion 12 will wrap substantially around one side and the back of the patient to come into engagement with first end portion 11 wherein the preferred fastening means comprising a hook and loop fastening system enables the patient to easily fasten the undergarment at the patient's side.

FIG. 2 is a perspective view of the front side 17 of the undergarment 10 of the present invention. Again, this embodiment shows first end portion 11 being somewhat shorter in length than second end portion 12 such that when positioned on the patient, the end portions will come together on the side of the patient where they may be easily fastened by the hook and loop fastening means shown in the figures.

Although specifically shown in the figures as hook and loop fasteners, the fastening mechanism utilized in the present invention could be any suitable securing means which allows the patient to easily engage and disengage the undergarment. For example, suitable fastening means include, but are not limited to, buttons, snaps, buckles, re-usable adhesive tape, etc.

The undergarment is constructed of an expandable material which is capable of conforming to the ever changing waistline of the CAPD patient, yet provide necessary support to hold the catheter in place against the patient. Particularly preferred materials include fabric blends and more particularly fabric blends which include at least some spandex fiber. A particularly preferred spandex is LYCRA ® spandex which is available from the DuPont Company.

Additionally, preferred materials which can be utilized in conjunction with spandex include, for example, cotton and/or nylon. In a preferred embodiment the undergarment comprises at least about 10 volume percent spandex. In one preferred embodiment the material comprises a fabric blend of about 10 volume percent spandex and about 90 volume percent cotton. In another preferred embodiment the undergarment comprises about 10 volume per cent spandex and about 90 volume per cent nylon. In a further preferred embodiment, the undergarment comprises about 10 volume percent spandex and about 90 volume percent of a combination of nylon and cotton.

By carefully choosing the proper fabric blend, which includes in a preferred embodiment at least some spandex, an undergarment can be provided with very desirable properties. Spandex has the ability to stretch to about five times its initial length and virtually instantaneously return to its original shape. By blending at least some spandex with either, for example cotton and/or nylon, a very desirable CAPD catheter support undergarment is obtained.

By utilizing at least some spandex, an undergarment is provided which easily conforms to the expanding waistline of the CAPD patient and is additionally very durable and comfortable. The undergarment can be worn in the shower and holds up well under repeated washings and drying. Since the undergarment is provided, in a preferred embodiment, by blending or weaving fabrics together by any known technique, the belt is easily manufactured to the various waist sizes of various patients. Additionally, the undergarment can be fabricated at a very low cost.

The pocket of the undergarment is designed to be sufficiently large as to substantially completely enclose the catheter, thus protecting the catheter from contacting and rubbing against the patient's clothes and skin. This assures the patient that the cap (or other means for closing off the catheter) of the catheter will not work its way free from rubbing against either the outer clothes or the skin of the patient.

As stated above, the pocket is located at the inner surface of the undergarment. In one embodiment the pocket is formed by attaching additional material, such as by sewing, to the inner surface material of the undergarment. When attaching the additional material, a portion of the additional material is not attached to the inner surface of the undergarment, thus forming the opening of the pocket to allow for placement of the catheter therein. In a second embodiment, the pocket may be formed by cutting or slicing a slit in the inner surface of the undergarment to form an opening between material forming the outer surface of the undergarment and material forming the inner surface of the undergarment. Other methods of forming a pocket at the inner surface of the undergarment should now be apparent to those skilled in the art.

In an additionally preferred embodiment, the pocket portion of the undergarment is provided to have a width wider than the width of the first and second end portions of the undergarment. Preferably the pocket portion has a width of about two inches and the end portions are provided in widths of about one inch. This provides for increased comfort of the patient since the pocket portion of the undergarment needs only be wide enough to comfortably secure and enclose the catheter. The end portions need only be provided in widths sufficient to secure the undergarment in place.

While the preceding description is merely exemplary in nature, many variations will become apparent to those of skill in the art. Such variations, of course, are included within the spirit and scope of this invention as defined by the following claims.

What is claimed is:

1. A continuous ambulatory peritoneal dialysis catheter support undergarment comprising:
    a belt of expandable material, wherein said expandable material includes about 10 volume percent of spandex fibers and about 90 volume percent cotton;
    said belt having a pocket portion made of said expandable material including an inner surface and an outer surface, and a first end portion and a second end portion;
    means for releasably attaching said first end portion to said second end portion; and
    a pocket formed by said expandable material for accepting said continuous peritoneal dialysis catheter located at said inner surface of said pocket portion.

2. The undergarment of claim 1, wherein said means for releasably attaching said first end portion to said second end portion are corresponding hook and loop fastening materials.

3. The undergarment of claim 1, wherein said first end portion is longer than said second end portion.

4. The undergarment of claim 1, wherein said pocket portion is wider than said first end portion and said second end portion.

5. A continuous ambulatory peritoneal dialysis catheter support undergarment comprising:
    a belt of expandable material, wherein said expandable material includes about 10 volume percent of spandex fibers and about 90 volume percent of a material selected from the group consisting of nylon and cotton;
    said belt having a pocket portion made of said expandable material including an inner surface and an outer surface, and a first end portion and a second end portion;
    corresponding hook and loop fastening materials distally located on said first end portion and said second end portion; and
    a pocket formed from said expandable material for accepting said continuous ambulatory peritoneal catheter located at said inner surface of said pocket portion.

6. A continuous ambulatory peritoneal dialysis catheter support undergarment comprising:
    a belt of expandable material, wherein said expandable material includes about 10 volume percent of spandex fibers and about 90 volume percent nylon;
    said belt having a pocket portion made of said expandable material including an inner surface and an outer surface, and a first end portion and a second end portion;
    means for releasably attaching said first end portion to said second end portion; and
    a pocket formed from said expandable material for accepting said continuous peritoneal dialysis catheter located at said inner surface of said pocket portion.

7. The undergarment of claim 6, wherein said means for releasably attaching said first end portion to said second end portion are corresponding hook and loop fastening materials.

8. The undergarment of claim 6, wherein said first end portion is longer than said second end portion.

9. The undergarment of claim 6, wherein said pocket portion is wider than said first end portion and said second end portion.

10. A continuous ambulatory peritoneal dialysis catheter support undergarment comprising:
    a belt of expandable material, wherein said expandable material includes about 10 volume percent or more of spandex fibers and the balance being a material selected from the group consisting of nylon and cotton;
    said belt having a pocket portion made of said expandable material including an inner surface and an outer surface, and a first end portion and a second end portion;
    means for releasably attaching said first end portion to said second end portion; and
    a pocket formed from said expandable material for accepting said continuous ambulatory peritoneal catheter located at said inner surface of said pocket portion.

* * * * *